(12) United States Patent
Sundara et al.

(10) Patent No.: US 9,327,054 B2
(45) Date of Patent: May 3, 2016

(54) NERVE GUIDE CONDUIT CONTAINING CARBON NANOTUBES

(75) Inventors: Ramaprabhu Sundara, Chennai (IN); Sathish Kumar Srinivasan, Vellore (IN)

(73) Assignee: INDIAN INSTITUTE OF TECHNOLOGY MADRAS, Chennai (IN)

( * ) Notice: Subject to any disclaimer, the term of this patent is extended or adjusted under 35 U.S.C. 154(b) by 921 days.

(21) Appl. No.: 13/202,941

(22) PCT Filed: Nov. 17, 2010

(86) PCT No.: PCT/IB2010/002922
§ 371 (c)(1),
(2), (4) Date: Aug. 23, 2011

(87) PCT Pub. No.: WO2012/004627
PCT Pub. Date: Jan. 12, 2012

(65) Prior Publication Data
US 2012/0109167 A1    May 3, 2012

(30) Foreign Application Priority Data
Jul. 9, 2010   (IN) .............................. 1963/CHE/2010

(51) Int. Cl.
*A61B 17/08*   (2006.01)
*A61L 27/50*   (2006.01)
*A61L 27/18*   (2006.01)
*A61B 17/00*   (2006.01)

(52) U.S. Cl.
CPC ................. *A61L 27/50* (2013.01); *A61L 27/18* (2013.01); *A61B 2017/00526* (2013.01); *A61B 2017/00871* (2013.01); *A61L 2430/32* (2013.01)

(58) Field of Classification Search
CPC ..... A61L 27/18; A61L 27/50; A61L 2430/32; A61B 5/6877; A61B 2017/00871
USPC .................................. 606/152; 607/116, 122
See application file for complete search history.

(56) References Cited

U.S. PATENT DOCUMENTS

| | | | | |
|---|---|---|---|---|
| 7,551,967 | B1* | 6/2009 | Karicherla et al. | 607/122 |
| 7,787,959 | B1* | 8/2010 | Morgan | 607/116 |
| 2007/0038307 | A1* | 2/2007 | Webster et al. | 623/23.5 |
| 2008/0299031 | A1* | 12/2008 | Liu et al. | 423/447.3 |
| 2009/0082856 | A1* | 3/2009 | Flanagan | 623/1.49 |

FOREIGN PATENT DOCUMENTS

WO    WO-2009/015287    1/2009

OTHER PUBLICATIONS

Hendricks, T.R. et al., "Processing of Loose Carbon Nanotubes into Isolated, High Density Submicron Channels", Nanotechnology, 2010, vol. 21, No. 115301, pp. 1-7.
International Search Report and Written Opinion for PCT/IB2010/002922 mailed Feb. 25, 2011.
(Continued)

*Primary Examiner* — Gregory Anderson
*Assistant Examiner* — Christina Lauer
(74) *Attorney, Agent, or Firm* — Foley & Lardner LLP (57) ABSTRACT

The embodiments herein relate to a conduit comprising an insulating material in a form of a tube having an inner surface and an outer surface, the inner surface having carbon nanotubes.

5 Claims, 9 Drawing Sheets

(56) References Cited

OTHER PUBLICATIONS

Nayak, T.R. et al., "Crucial Parameters Responsible for Carbon Nanotubes Toxicity," Current Nanoscience, 2010, vol. 6, pp. 141-154.

Bian, Y.Z. et al., "Evaluation of poly(3-hydroxybutyrate-co-3-hydroxyhexanoate) conduits for peripheral nerve regeneration," Biomaterials, vol. 30, No. 2, pp. 217-225 (Jan. 2009).

Jiang, X., et al., "Current applications and future perspectives of artificial nerve conduits," Experimental Neurology, vol. 223, No. 1, pp. 86-101 (May 2010).

Lin, Y.L., et al., "Sciatic nerve repair by microgrooved nerve conduits made of chitosan-gold nanocomposites," Surgical Neurology, vol. 70, No. 1, pp. S9-S18 (Dec. 2008).

MacDonald, R. A., et al., "Carbon nanotubes increase the electrical conductivity of fibroblast-seeded collagen hydrogels," Acta Biomater, vol. 4, No. 6, pp. 1583-1592 (Nov. 2008).

Mao, C., et al., "New biocompatible polypyrrole-based films with good blood compatibility and high electrical conductivity," Colloids Surfaces B Biointerfaces, vol. 67, No. 1, pp. 41-45 (Nov. 15, 2008).

Oh, S.H., et al., "Peripheral nerve regeneration within an asymmetrically porous PLGA/Pluronic F127 nerve guide conduit," Biomaterials, vol. 29, No. 11, pp. 1601-1609 (Apr. 2008).

Wang, S., et al., "A new nerve guide conduit material composed of a biodegradable poly(phosphoester)," Biomaterials, vol. 22, No. 10, pp. 1157-1169 (May 2001).

* cited by examiner

NERVE GUIDE CONDUIT CONTAINING CARBON NANOTUBES

CROSS-REFERENCE TO RELATED APPLICATIONS

The present application is a U.S. national stage application claiming the benefit under 35 U.S.C. §371 of International Application No. PCT/IB2010/002922, filed on Nov. 17, 2010, which claims priority to Indian Patent Application No. 1963/CHE/2010, filed on Jul. 9, 2010, the entire contents of which are incorporated herein by reference in their entirety.

BACKGROUND

Nerve injuries occur through accidents, idiopathic damage, iatrogenic injuries, compression syndromes and systemic diseases. Therefore, restoration of severed nerve pathways is desirable. One approach for restoration of severed nerve pathway is with nerve regeneration emulated by a biocompatible nerve guide conduit. To address this requirement, biologically compatible synthetic nerve guide conduits have been used to connect severed nerve stumps. The conduit can provide cues to stimulate nerve regeneration and facilitate the growth of the nerve.

Different types of biologically compatible materials have been used for the preparation of nerve guide conduits, including biodegradable and non-biodegradable biopolymers. The application of external electric current to the nerve guide conduits can expedite the nerve regeneration process. The biomaterials for nerve guide conduits have been engineered to provide electrical conductivity and electrical contacts for external manipulations of nerve growth. Conducting polymers like polypyrrole, chitosan, polyesters and cellulose have been used for preparing nerve guide conduit.

SUMMARY

An embodiment relates a conduit including an insulating material in a form of a tube having an inner surface and an outer surface, the inner surface having carbon nanotubes. In one aspect, the conduit is a nerve guide conduit. In another aspect, the conduit has an electrical conducting property in a semi-conducting range at ambient conditions. In another aspect, the conduit is configured to direct an electric current from a first end of the conduit attached to a nerve stump to a second end of the conduit without a substantial leak in the electric current. In another aspect, the insulating material includes silicone.

In another aspect, the carbon nanotubes include functionalized carbon nanotubes. In another aspect, the functionalized carbon nanotubes have carboxyl and hydroxyl functional group on a surface of the functionalized carbon nanotubes. In another aspect, a surface of the conduit has a water contact angle of greater than 90 degrees.

Another embodiment relates to a method including forming a conduit of an insulating material, the conduit having an inner surface and an outer surface, and forming a coating of carbon nanotubes on the inner surface. In one aspect, forming the conduit includes pouring a precursor of the insulating material in a mold and heating the precursor to form the insulating material shaped as the conduit. In another aspect, forming the coating of carbon nanotubes on the inner surface includes preparing a layer of carbon nanotubes and coating the layer of carbon nanotubes on the inner surface. In another aspect, forming the coating of carbon nanotubes on the inner surface includes functionalizing the layer of carbon nanotubes.

In another aspect, the insulating material includes silicone. In another aspect, the carbon nanotubes include functionalized carbon nanotubes having carboxyl and hydroxyl functional group on a surface of the functionalized carbon nanotubes. In another aspect, a surface of the conduit has a water contact angle of greater than 90 degrees.

Another embodiment relates to a method of treating nerve disorder including placing a conduit made of an insulating material in a severed nerve pathway, wherein the conduit has an inner surface and an outer surface, the inner surface having carbon nanotubes. In one aspect, the conduit has an electrical conducting property in a semi-conducting range at ambient conditions. In another aspect, the conduit is configured to direct an electric current from a first end of the conduit attached to a nerve stump to a second end of the conduit without a substantial leak in the electric current. In another aspect, the insulating material comprises silicone. In another aspect, the carbon nanotubes include functionalized carbon nanotubes having carboxyl and hydroxyl functional group on a surface of the functionalized carbon nanotubes.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE FIGURES

FIG. 2 shows Raman spectroscopy (A) and thermogravimetric analysis (B) of an illustrative embodiment of carbon nanotube (CNT).

FIG. 3 shows X-Ray diffractogram of illustrative embodiments of (A) CNT and (B) polydimethyl siloxane (PDMS).

FIG. 4 shows IR spectrum of illustrative embodiments of (A) CNT and functionalized CNT and (B) electrical conductivity of PDMS-CNT.

FIG. 5 (A) shows water contact angle of the CNT surface of an illustrative embodiment of PDMS-CNT film and (B) shows a water droplet placed on the CNT surface of the PDMS-CNT film.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

An embodiment relates to a conduit comprising an insulating material in a form of a tube having an inner surface and an outer surface, the inner surface having functionalized carbon nanotubes. Other embodiments relate to a method comprising forming a conduit of an insulating material, the conduit having an inner surface and an outer surface, and forming a coating of functionalized carbon nanotubes on the inner surface. Yet other embodiments relate to a method of treating nerve disorder comprising placing a conduit made of an insulating material in a severed nerve pathway, wherein the conduit has an inner surface and an outer surface, the inner surface having functionalized carbon nanotubes.

For example, an illustrative embodiment relates to a flexible, and transparent nerve guide conduit (NGC) comprising a tube of poly-dimethyl-siloxane (silicone), which is an insulating material, and having functionalized nano composite material such as carbon nanotubes (CNT) coated inside the tube. The coated CNT perform the role of conducting electric signals parallel though the nerve guide conduit. The nerve guide conduit using the nanocomposite material can have an electrical conducting property in the semiconducting range ($10^{-1}$ S/m) at ambient conditions.

The term "nerve guide conduit" is defined as either a biological or synthetic hollow tube responsible for bridging the gap between the proximal and distal stumps of a severed nerve during tubulization of nerve injury. Nerve guide conduits are generally classified as biological (autogenous and non-autogenous) and non-biological conduits. The most widely recognized autogenous biological tubes for bridging peripheral nerve defects are vein and skeletal muscle. Collagen tubes are used as non-autogenous biological conduits for successful nerve regeneration. Example categories of non-biological or synthetic conduits include absorbable and non-absorbable conduits. Synthetic conduits are used as neuroprosthetic implants for nerve repair both in clinical and preclinical studies. Nonabsorbable conduits include expanded polytetrafluoroethylene (Gore-Tex tubes), and silicone tubes. Absorbable conduits include polygalactin and polyglycolic acid tubes. Tissue engineered conduits (nerve/vein combined graft and muscle/vein graft) and other biocompatible synthetic conduits include silicone enriched with nerve growth factor, ciliary neurotrophic factor, glial growth factor, and Schwann cells. Conducting polymers such as polyaniline and polypyrrole can be used for neuron regeneration application because of its electrical and mechanical properties. Currently marketed nerve conduits are Neurotube [Synovis], Neurolac [Ascension], SaluBridge [SaluMedica], and NeuraGen [Integra].

Silicone tube can be used as a chamber for a nerve guide conduit used in the tubulization of peripheral nerve gap injuries. Typically, the length of the gap between nerves successfully bridged ranges from 5 mm to 30 mm in patients. The non-biodegradable conduits like silicone generally require a secondary surgery to remove the implant. On the other hand, the biodegradable conduits such as poly glycolic acids and poly lactic acids, polyesters and its copolymers requires proper engineering of the material, because it should remain intact for the time period during which axons need to regenerate across the nerve gap and then degrade gradually with minimal swelling and foreign body reaction. It should also exhibit sidewall erosion instead of bulk erosion, because bulk erosion of polymer from the implants can cause undesirable environment, such as immunogenic risks, for nerve regeneration. Therefore, vein, muscle, and synthetic material tubes such as silicone tubing, polyglycolic acid tubes, and combinations of these conduits can be more successful alternates to autogenous nerve grafting.

A suitable synthetic material tube should generally provide appropriate cues for nerve regeneration. For enhanced axonal regeneration, a manifold of cues include topographical (rough, smooth, stripe, micro or nano patterns, 2D, and 3D networks), mechanical (biodurability, and tensile strength), biochemical (presence of Schwann cells, glial cells, neural stem cells, growth factors, collagen, laminin) and electrical (presence of medium to electrically stimulate neurons for enhanced axonal regeneration) stimuli. These cues mimic the native extracellular matrix, to provide better contact guidance on neurite outgrowth and also to promote cell adhesion, viability and proliferation of neurons. The illustrative bioengineered nerve guide conduits of the embodiments herein use modified silicone nerve guide conduits, for example, which can confer electrical, mechanical and biochemical cues.

The nerve guide conduit of the embodiments can have multi-function modalities including electrical conducting property, flexibility, biocompatibility, growth factor delivery and mechanical strength. The tubular implants can possess these multifunctional modalities thereby facilitating the communication between the proximal and distal nerve stumps.

The term "electrical conductivity" refers to the ability of a material to conduct electricity. This property is one of the desired properties of a nerve guide conduit because electrical stimulation of a nerve results in the creation of a pathway for direct electrotonic current (a current induced in a nerve sheath without the generation of new current by an action potential) transfer, which in turn cause a redistribution of charge along the surface of the nerve membrane. This membrane potential or transmembrane voltage affects the voltage-dependent membrane processes leading to action potential of the nerve. Typically, −15 mV above the resting membrane potential (−70 mV) is sufficient to achieve critical threshold potential required to initiate nerve action potential.

In example embodiments herein the nerve guide conduits can comprise, for example, silicone tubes with CNT coating, which can have conductivity on the order of about $10^{-1}$ S/m, collagen tubes, which have conductivity on the order of $10^{-4}$ S/m, and Poly(D, L-lactide-co-ε-caprolactone), an insulating polymer tuned with electrical conducting property upon coating with polypyrrole to have an electrically conducting polymer of conductivity of $10^{-3}$ S m$^{-1}$.

The term "flexibility" refers to kink resistance (i.e., the maximum angle of bending without kinking). This property is one of the desired properties of a nerve guide conduit for nerve repair because the nerve ends might not be in the same plane/line and the gap to be bridged might cross a joint. Kink resistance can be measured by bending the tube to 180° and on release it should have the capability to bring back to its original shape without the formation of a crease or kink. A high kink resistance provides bending of the conduit for proper connections such as nerve repair in wrists and hands. If the kink resistance is low, then it can cause nerve compression, axonal disruption and neuroma formation.

The term "biocompatibility" of a nerve guide conduit refers to the ability of the nerve guide conduit to exist alongside nerves and other living tissues without harming them. Biocompatibility of novel polymer implantable materials can be evaluated by performing in vitro biocompatibility assay or cell viability and proliferation assays in comparison with silicone polymer as the standard or primary reference material (PRM). Since 1984, silicone has been considered as the reference tool for the validation of in vitro and in vivo tests by the National Heart, Lung, and Blood Institute in USA.

In example embodiments, a nerve guide conduit using carbon nanotubes and silicone polymer for nerve repair application, neovascularization (i.e., formation of functional microvascular networks with red blood cell perfusion) and angiogenesis (i.e., formation of new blood vessels) were the two biocompatibility characteristics used to substantiate the biocompatibility of nerve guide conduits both in vitro and in vivo tests. Carbon nanotubes can provide neuronal electrical signaling and are compatible with mammalian and neuronal cells resulting in enhanced neurite outgrowth. A carbon nanotube coating over silicone can improve cellular proliferation. In addition, silicone with a carbon nanotube coating can have improved cell adhesion, thereby avoiding adverse effects of silicone such as formation of fibrous capsules, development of contractures and displacement during the course of long term usage. Thus, the biocompatibility of a carbon nanotube coating on silicone makes a nerve guide conduit of silicone tube with carbon nanotubes coating a promising component of neuroprosthetic implants to improve the neuronal regenerative ability of synthetic nerve guide conduits.

The term "growth factor" refers to a naturally occurring substance capable of stimulating cellular growth, proliferation and cellular differentiation. Growth factors typically act as signaling molecules between cells. Several growth factors include nerve growth factor (NGF), glial cell-line derived neurotrophic factor (GDNF), and ciliary neurotrophic factor (CNTF), brain-derived neurotrophic factor (BDNF), neurotrophin-3 (NT-3) and others have a role in the neural development. Hence, loading these factors in the nerve guide conduit would enrich the entubulization approach of nerve repair. However, severe adverse events can occur due to a high concentration of these factors at the site of nerve injury, requiring a controlled delivery of growth factors for getting enhanced neuron regeneration. There are many techniques to estimate the appropriate amount of growth factors to be loaded in the conduits. These techniques include high performance liquid chromatography and in vitro growth factor release assays. The addition of supportive cells such as Schwann cells, glial cells, neural stem cells etc. into the nerve tube can modulate the intrinsic mechanisms to promote axonal outgrowth, and also enhance the functionality of nerve guide conduits. Schwann cells can enhance nerve regeneration by different mechanisms including secretion of adhesion molecules (L1 and neural cell adhesion molecule (N-CAM)), extracellular molecules (collagen and laminin) and a number of tropic factors such as NGF, BDNF and NT-3. The Schwann cells can be seeded into a silicone conduit before securing the conduit to the proximal and distal nerve stumps with sutures.

The term "mechanical strength" of a nerve guide conduit refers to the ability of the nerve guide conduit to withstand suturing, remain intact after surgery, and provide proper guidance and support of the regeneration of severed nerve. The tensile strength of the synthetic nerve conduit can be evaluated by measuring the suture pullout strength in grams using a tensile tester, in which the suture is placed through the edge of the conduit followed by tying the suture to a hook adapter of a tensile tester. Then the conduit is pulled at a speed of 1.0 in/min until the suture is pulled out. The qualitative method for evaluating mechanical properties such as elasticity and resistance to tearing when applying traction to the suture can be performed by checking the ease of making sutures on nerve guide conduits with a polyamide wire (Ethilon 11/0). A qualitative score from 1 to 4 (bad-moderate-good-very good) was given and the one that exhibits an average of 3 and above was considered as acceptable nerve guide conduit.

In an embodiment, a nerve guide conduit directs the electrical stimulus generated at the nerve stumps in a single direction and without substantial leak in electric current. At the time of electrical stimulation of nerve, the nerve guide conduit can engender a pathway allowing direct electrotonic current (a current induced in a nerve sheath without the generation of new current by an action potential) transfer which in turn causes a redistribution of charge along the surface of the neuronal membrane. The applied direct current (mA) during direct (electric current applied on the nerve) and indirect (electric current applied at places other than nerve) electrical stimulation should not leak out through the nerve guide conduit attached between the proximal and distal stumps of severed nerve ends. For example, if the nerve guide conduit was made up of conducting (polypyrrole-PPY) or semi conducting materials (collagen conduits), then there is a possibility of the distribution of current through the nerve guide conduit in different directions to the adjoining muscles and other tissues. This wastage of current would directly affect the generation of electrotonic current necessary for neuron regeneration.

In an example embodiment, a nerve guide conduit has two layers including an outer insulating layer and an inner conducting layer. The two layered nerve guide conduit can obviate unnecessary twitching of muscles and contractions of other tissues adjoining the nerve implant during external application of electric current. Hence, a reinforcement of direct coupling of neurons can be achieved using nerve guide conduits that direct the electrical stimulus generated at the nerve stumps in a single direction and without substantial leak in electric current such that there is less than about 10% leak in the current though the insulating conduit of the nerve guide.

In an example embodiment, the nerve guide conduit was prepared by a facile technique. Nerve guide conduits can be prepared by several techniques known to persons skilled in the art, which include dip coating of a rotating mandrel, precipitation on a rotating mandrel, phase inversion of a rotating teflon mandrel, and rolling of a mesh.

Silicone is an insulating polymer having properties such as hydrophobicity and physiological inertness. A pre-polymer solution of silicone is generally viscous and produces froth and air bubbles when the monomers are treated with the curing agent. In addition, the polymerization of silicone monomers occurs at a temperature between 80-120° C.; hence, requiring thermosetting of the silicone tubes. In addition, in one embodiment, the synthetic conduit can have two layers (insulating and conducting) physically attached together, while in another embodiment mixing the conducting component into the insulating component may be performed in a rotating mandrel or melt extrusion methods can produce a single layer with both insulating and conducting materials therein. Further, casting the silicone in a mold is one method that may be used to prepare thermosetting silicone conduits.

Figure 1:
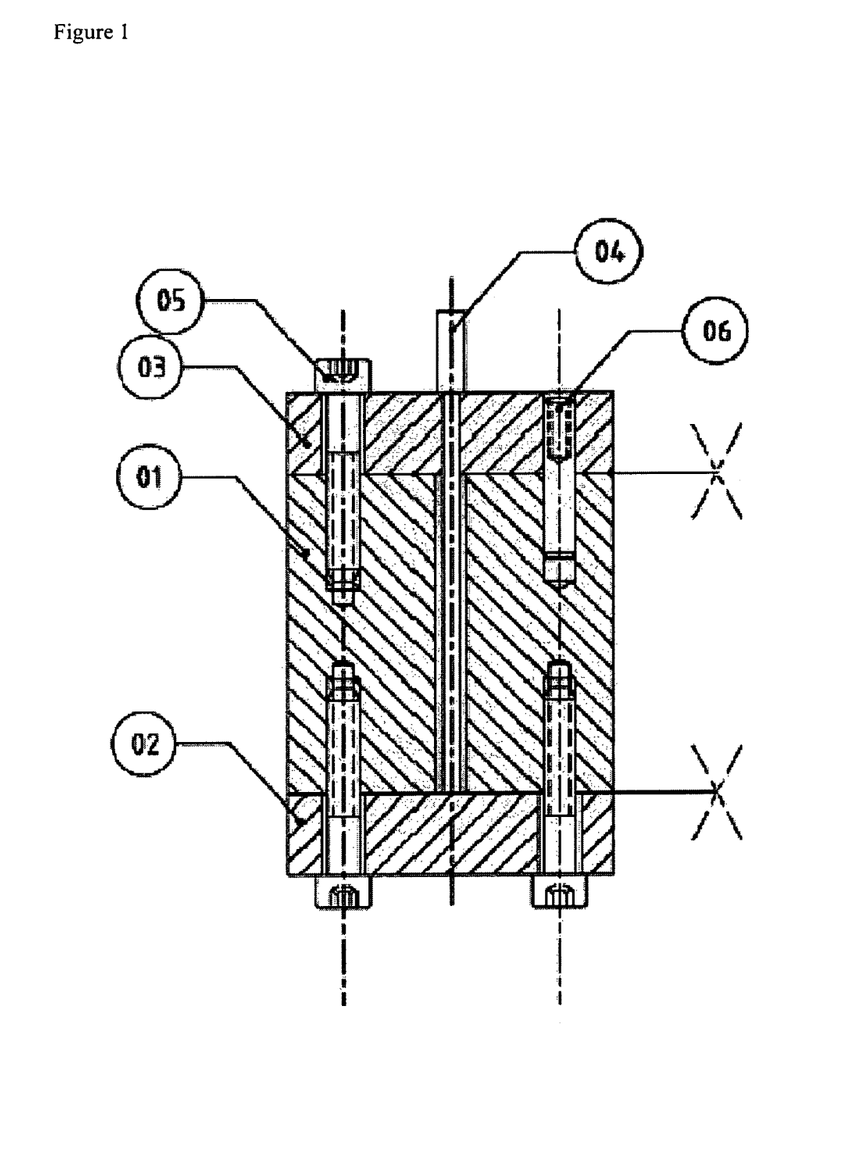
FIG. 1 shows an illustrative embodiment of the mold for making a silicone conduit.

One aspect of the embodiments relates to the mold used for the preparation of NGC and the method developed to prepare NGC having two layers such as an insulating silicone layer on the outside and a conducting CNT layer on the inside of the hollow silicone tube. An illustrative embodiment of the mold is shown in FIG. 1. The mold comprised three P20 steel pieces: a top core plate (03), a cavity plate (01) and a bottom plate (02). The top core plate and the bottom plate may be joined to the cavity plate of the mold using screws (05). A dowel (06) is shown in one of the holes through which a screw (05) can be inserted to join the pieces of the mold. A core pin (04) may be inserted through the top core plate into the cavity plate (01) through a small groove made in the top core plate (03) so as to hold the core pin (04) in a vertical position. The outer diameter of the core pin (04) was equal to the inner diameter of the nerve guide conduit. The length of the cavity plate (01) was equal to the desired length of the nerve guide conduit. A polyimide sheet may be rolled inside the cavity to remove the finished conduit out of the cavity easily without sticking to the insider surface of the cavity in the cavity plate (01). However, if the cavity plate (01) was into two halves such that two halves can be separated after the nerve guide conduit is formed, then the use of the polyimide sheet would not be required. This modification of the cavity plate (01) of mold may be applied to conditions with large scale preparation of nerve guide conduits.

Example steps involved in the preparation of an embodiment of a nerve guide conduit include: assembling the bottom plate and the cavity plate of the mold, inserting the core pin into the cavity plate, filling the silicone pre-polymer solution in the space between the core pin and the cavity in the cavity plate, inserting the core pin in the cavity, closing the cavity with the top core plate on top of the cavity plate, polymerizing the silicone pre-polymer, removing the top core plate and the core pin, removing the bottom plate, removing the silicone conduit from the cavity along with the polyimide sheet, and separating the polyimide sheet from the silicone conduit.

In one embodiment, after the fabrication of the insulating conduit, the NGC was prepared by coating a thin layer of a conducting nano-material such as CNT inside the insulating conduit such as the silicone conduit. For example, the coating of CNT inside the hollow silicone conduit was performed by forming a thin film containing functionalized carbon nanotubes having a thickness of about 1 µm. The thin film formation was carried out by sonicating 30 mg of CNT in 10 ml of toluene for 15 minutes using a bath ultrasonicator, followed by vacuum filtration using a cellulose nitrate filter (Sartorius AG, Germany) having a pore size of 0.2 µm. Then the filter membrane containing CNT was dried under vacuum at 40° C. for 16 hours. After complete drying, the CNT film was peeled off easily from the filter membrane.

Alternatively, the CNT films were prepared by putting the ultrasonicated solution on a clean, dry silicon wafer and allowing the toluene solvent to gradually evaporate under vacuum at ambient temperature. The thickness of the CNT film can be in the range from 1-2 µm.

It was observed that a thin CNT film formed on the silicon wafer was more easily peeled off than the CNT film formed on the filter membrane. This ease of peeling off effect was attributed to the smooth surface of silicon wafer compared to the filter membrane. CNT thin films were rolled in the form of tubes over a thin teflon rod having the outer diameter less than the inner diameter of the silicone nerve guide conduit. When the silicone nerve guide conduit was separated from the mold, a teflon rod containing CNT film roll was immediately transferred into the hollow silicone tube. The teflon rod was rolled inside the silicone tube to exert little pressure in order to print the CNT layer over the silicone inner surface followed by removal of excess CNT from the silicone tube. It was observed that the CNT coating should be performed immediately when the silicone conduit was hot and fresh. The adhesive property of silicone with carbon nanotubes may be attributed to the low-energy surfaces of silicone having intermolecular forces between organic (two methyl groups) and inorganic (siloxane) molecules.

Subsequently, the morphology, crystallinity, chemical nature, purity, and molecular vibrations were characterized using electron microscope, X-ray diffractograph, infra-red spectroscopy, thermogravimetric analysis and Raman spectroscopy. In an embodiment, the electrical conductivity, water contact angle and crystallinity of silicone nerve guide conduit, functional groups, molecular vibrations and morphology were characterized using four probe electrical conductivity with a physical property measurement system (PPMS), contact angle measuring instrument and X-ray diffractograph, PPMS, XRD, IR, Raman spectroscopy, TEM and HRTEM techniques.

In one embodiment, the amount of carbon nanotubes in the coating layer was less than 1 weight % of the total weight of the NGC to achieve the electrical conductivity. In one embodiment, the nerve guide conduit having CNT conducting layer and silicone insulating layer were stuck together by the physical adhesive force of silicone. Thus, the nerve guide conduit had two separate conducting and insulating layers, thereby decreasing the amount of CNT required for electrical conductivity and simultaneously improving the efficiency of the nerve implant for providing mechanical and electrical cues required for nerve regeneration.

The NGC of the embodiments can be tested in the severed nerves of human or animal (e.g., rat sciatic nerve), and nerve growth factors, with drug and other immunomodulators can be incorporated in the silicone-CNT during the preparation of the conduits. Silicone has been used as a nerve regeneration chamber, both in animal and clinical studies. So a NGC made of a silicone conduit with CNT coated on the inner wall of the silicone conduit would be acceptable both in the animals and patient studies because both silicone and CNT have been reported to have good biocompatibility.

In some embodiments, a modified silicone nerve guide conduit having nerve growth factors can be made using the NGC of the embodiments because the nerve growth factors can be attached to the functional groups of CNT. Nerve growth factor attached to the CNT can result in enhanced nerve regeneration and thus the NGC of these embodiments can provide a possible means to render biochemical cues to the severed nerves. In addition, an enriched environment within the NGC of the embodiments can also be achieved by filling the NGC with Schwann cells and Stem cells within the hollow space of the conduit for nerve regeneration.

EXAMPLES

Synthesis of Carbon Nanotubes

Synthesis of carbon nanotubes was performed by a chemical vapor deposition (CVD) method disclosed in T. R. Nayak, et al., *Current Nanoscience* 2010, 6, 00, which is incorporated herein in its entirety by reference. The synthesis steps include: catalyst preparation and growth of nanotubes. The growth process involved heating of catalyst material to high temperatures (500-850° C.) in a furnace under a constant flow of hydrocarbon gas (acetylene) through the reactor over a period of time. Iron, nickel or cobalt containing alloy hydride fine particles were used as catalysts. The purification of carbon nanotubes was performed by acid treatment followed by air oxidation at 350° C. for 2 hours. 1 gm of purified carbon nanotubes was taken in a round bottom flask and 40 ml of concentrated nitric acid was added and refluxed for 10 hours, followed by decantation with distilled water to remove nitric acid. The residue was dried and stored for further studies.

Functionalization of CNT was carried out after the purification of CNT in accordance with the teaching in T. R. Nayak, et al., *Current Nanoscience* 2010, 6, 00, which is incorporated herein in its entirety by reference. Briefly, biological functional groups such as carboxylic acid and hydroxyl groups were introduced on the surface of CNT upon treatment with concentrated nitric acid and concentrated sulfuric acid in the ratio of 1:3. The purpose of utilizing functionalized CNT instead of pristine CNT was that the cytotoxicity of pristine CNT was significantly reduced or nullified by introduction of functional groups without affecting the aspect ratio of CNT.

Preparation of Silicone Conduit

Dimethyl siloxane and curing agent Sylgard 184 (other similar curing agents are 4280 kettle resin, m-phenylenediamine, N-phenyl-beta-naphthylamine, dibetanaphthyl-p-phenylene diamine, colloid calcium carbonate, polyisoprene, silicone rubber) were taken in a small vial in the ratio of 10:1 and vigorously stirred and transferred to vacuum desiccators to remove the air bubbles. A polyimide sheet was placed on the inside surface the mold. A clear viscous solution of dimethyl siloxane and curing agent was carefully poured into the mold described above for making the silicone conduit. The mold was placed inside a vacuum oven at 80° C. for 20 minutes. The silicone conduit was then removed from the mold. A very thin layer of CNT film was prepared as described above. Subsequently, this thin layer of CNT film was coated on the inside surface of the hollow silicone conduit. The silicone tubes had internal and external diameters of 3 mm and 6 mm, respectively. However, the internal and external diameters of the silicone tube can vary from about 1-10 mm and 2-20 mm, respectively, for example.

Characterization of the Silicon-CNT Tubes

Figure 2A:
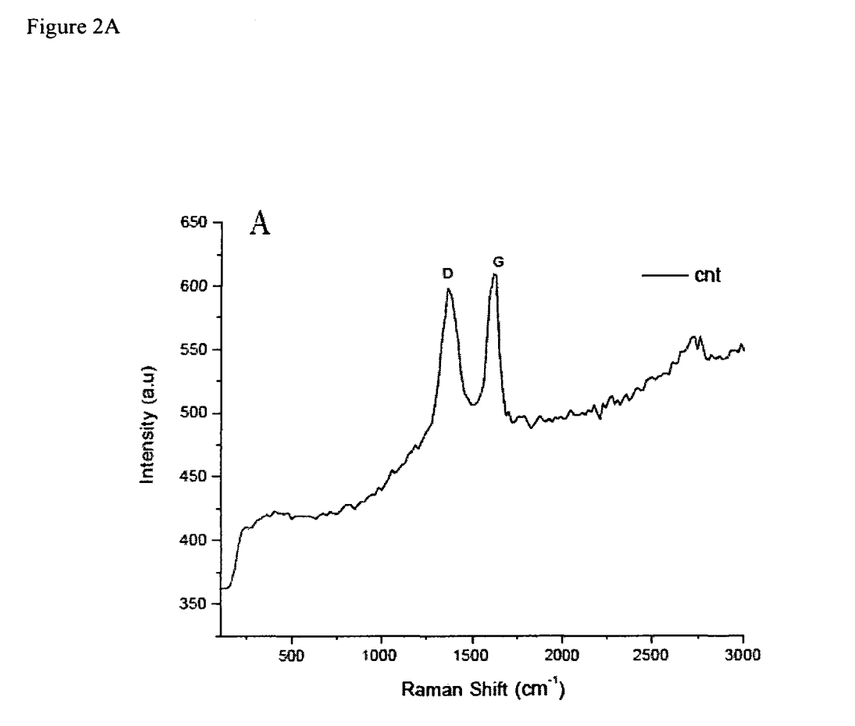
Figure 2B:
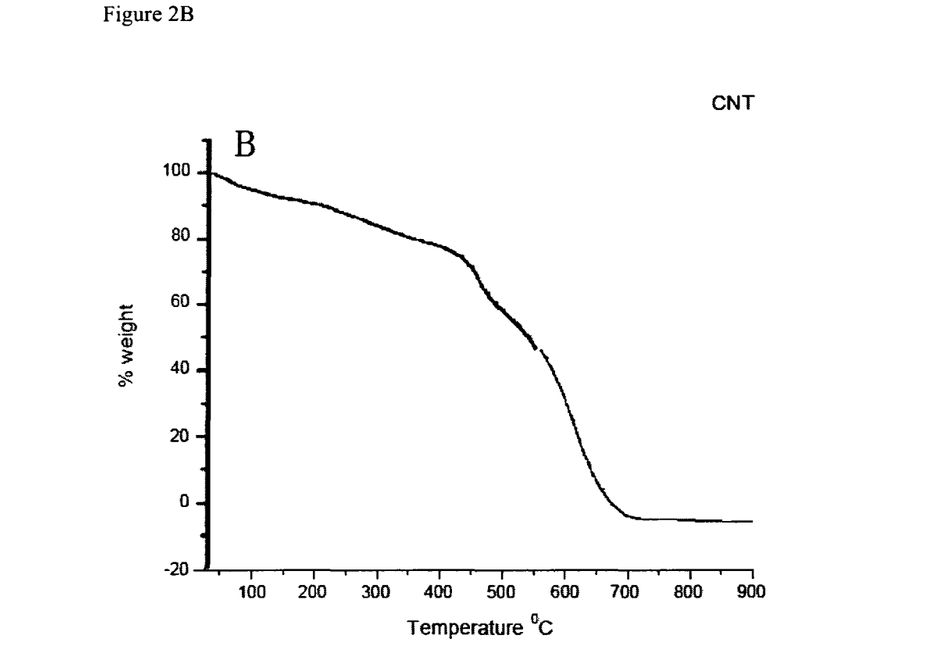

Morphological properties of the silicone-CNT conduit were determined using transmission electron microscopy and scanning electron microscopy. CNT has 30-50 nm internal diameters and 100 µm in length. FT-Raman Spectroscopy studies were carried out using an excitation wavelength of 1064 nm with Nd-YAG laser. CNT showed D-band at 1363 $cm^{-1}$ which was attributed to the defects created along the nanotube surface during the vigorous acid treatment. The G-band (1616 $cm^{-1}$) showing tangential modes corresponding to the Raman allowed optical mode of two-dimensional graphite (FIG. 2A). Thermogravimetric analysis of CNT indicated a slight weight loss observed below 500° C. for purified carbon nanotubes which was due to the burning of amorphous carbon. Weight loss between 500° C. and 700° C. was assigned to the burning of CNT. Final residual weight of 1.5% was obtained for the purified CNT. The purity of the purified sample was about 95% (FIG. 2B).

Figure 3A:
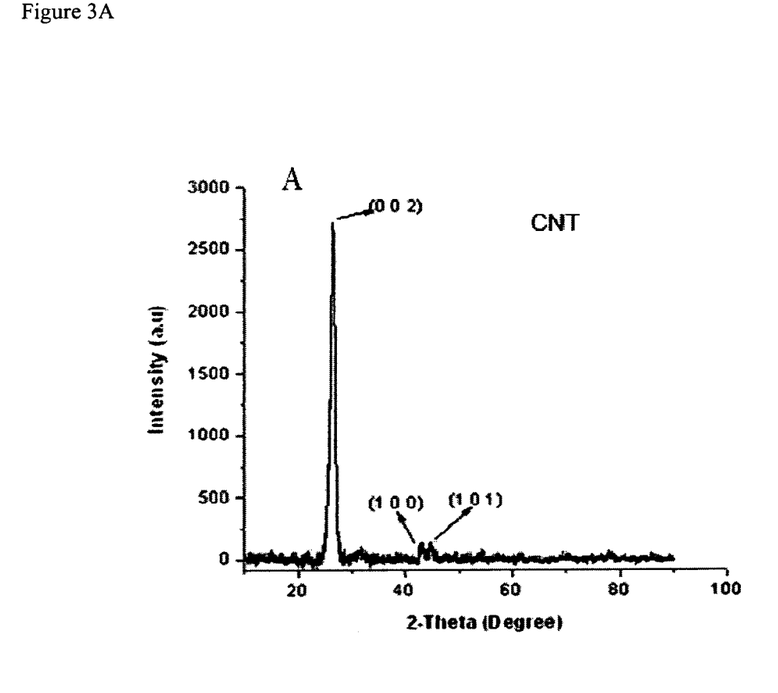
Figure 3B:
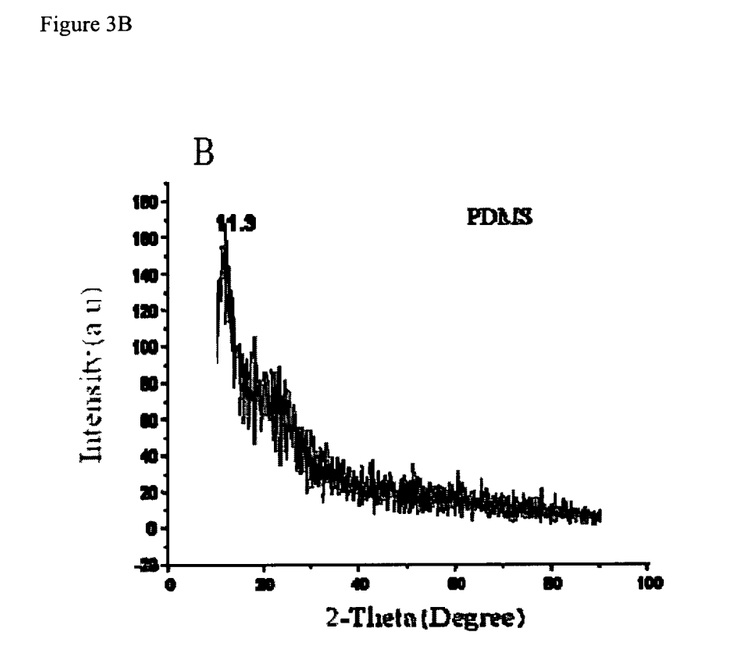

The crystalline property of CNT was identified using X-ray diffractogram with X-rays obtained from Cu Kα at 40 KV. The CNT had 2θ values at 26 and 43 (FIG. 3A). A film made of the silicone of the silicone-CNT tube had a crystalline nature having 2θ value between 10°-15° (FIG. 3B).

Figure 4A:
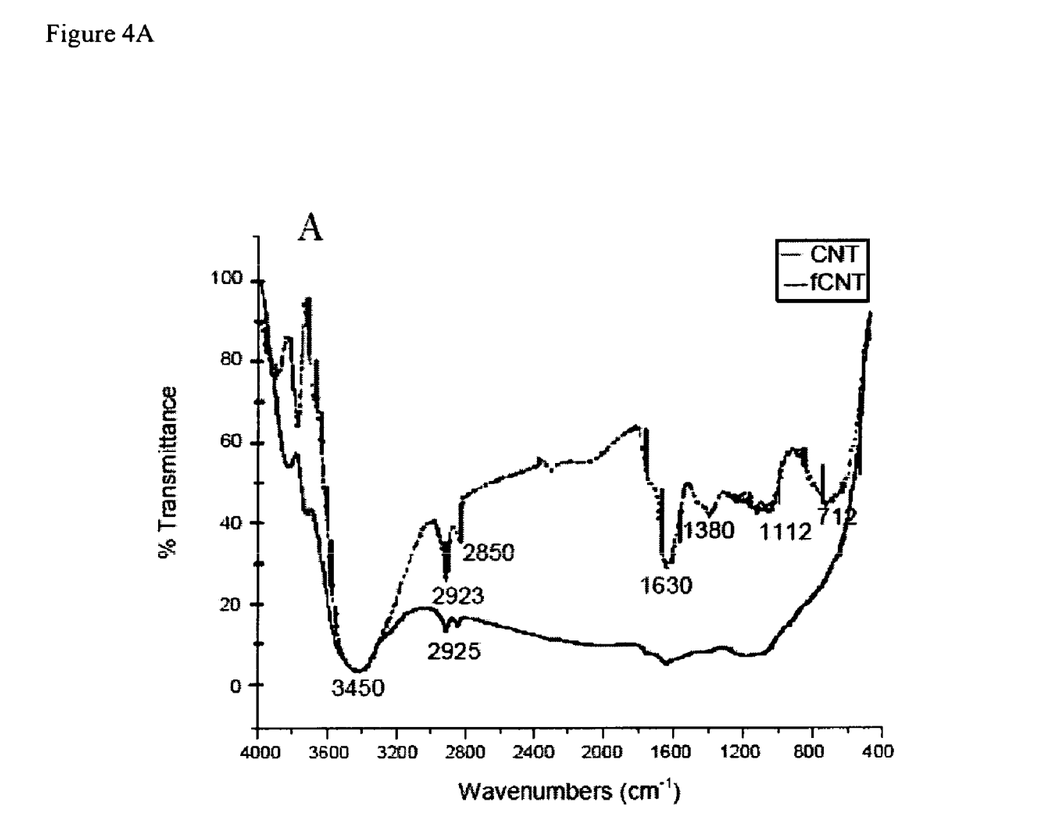

The functional groups of CNT were identified using FT-Infra-red Spectrometric-KBr pellet technique. Infra-red spectrum of CNT and functionalized CNT were obtained and the vibrations of the functional groups of f-CNT were clearly observed as shown in FIG. 4A and these values were compared with the fundamental vibrations of functional groups. Inclusion of carboxyl and hydroxyl functional group on the surface of f-CNT were observed which were absent in the pristine CNT (Table 1).

TABLE 1

Interpretation of IR Spectrum of CNT and fCNT

| Wavenumber ($cm^{-1}$) | Wavelength (µm) | Functional groups | Type of Vibrations |
| --- | --- | --- | --- |
| 3450 | 2.898 | —OH group | O—H Stretching |
| 2925 | 3.418 | — | —C—H Stretching superimposed upon —O—H stretching |
| 2923 | 3.421 | — | —C—H stretching superimposed upon —O—H stretching |
| 2850 | 3.508 | Aldehydes | —C—H stretching |
| 1630 | 6.134 | Aldehydes and ketones | —C=O stretching |
| 1380 | 7.246 | Gem dimethyl group | —C—H group |
| 1112 | 8.992 | Ethers | —C—O stretching in C—O—C group |
| 712 | 14.04 | Mono-substituted benzene | —C—H bending |

Figure 4B:
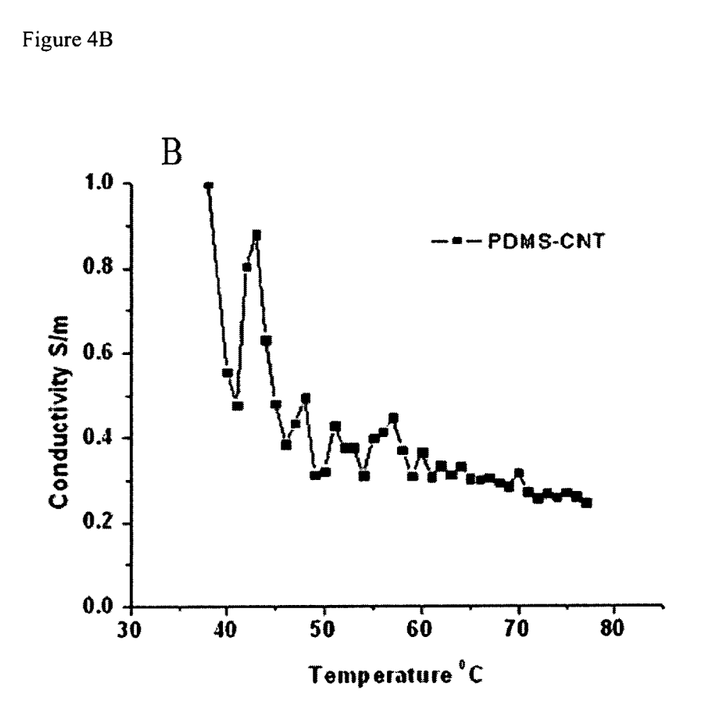

The four wire contact technique using a PPMS instrument made by Physical Property. Measurement System from Quantum Design, USA, was performed to determine the conductivity of silicone-CNT conduit. A small portion of NGC was fixed over a golden puck having four wires soldered to provide electrical contacts. Then the puck was loaded into a holder followed by lowering in to a chamber for purging with helium. Then, a constant current of 0.005 µA was applied between two adjacent corners and the voltage across the remaining two corners was measured at the temperature range 300-350 K with an increment rate of 5K/min. The resistivity was obtained from the recordings. The electrical conductivity of silicone-CNT at 37° C. was shown to have $3\times10^{-1}$ S/m which lies in the semiconducting range (FIG. 4B).

The silicone-CNT conduit had less than 1 wt % of CNT coated inside the silicone tube. The water contact angle measurement could be performed on a uniform thickness film kept on the platform of the instrument. So, a film having different concentration of CNT films coated on the silicone layer were prepared. Then a water contact angle was measured using a contact angle measurement goniometer (Kruss, Germany). The silicone-CNT film was mounted on the substrate followed by addition of four drops of water using a hypodermic syringe. The angle between the solid and the liquid interface was observed from the computer display and an average of the triplicate values of contact angle was taken to verify the hydrophilic or hydrophobic nature.

Figure 5A:
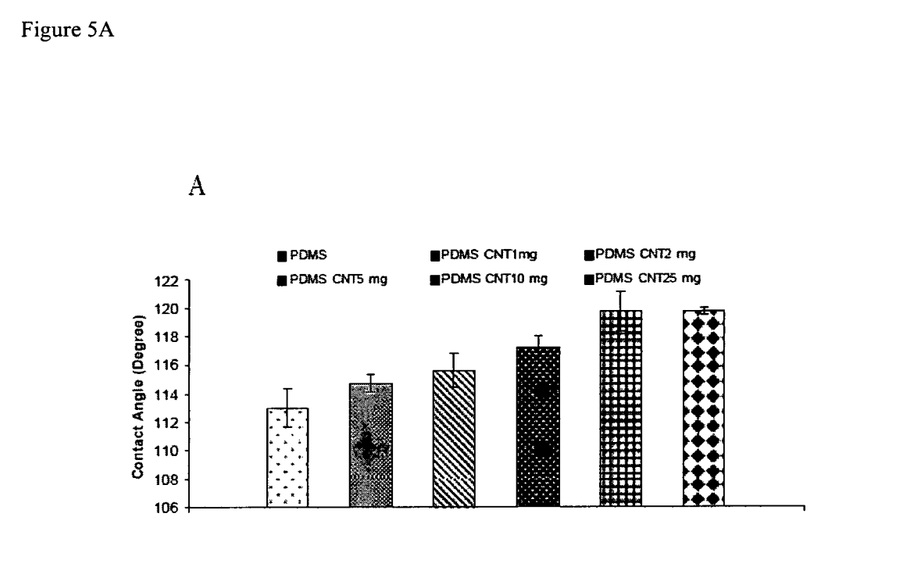
Figure 5B:
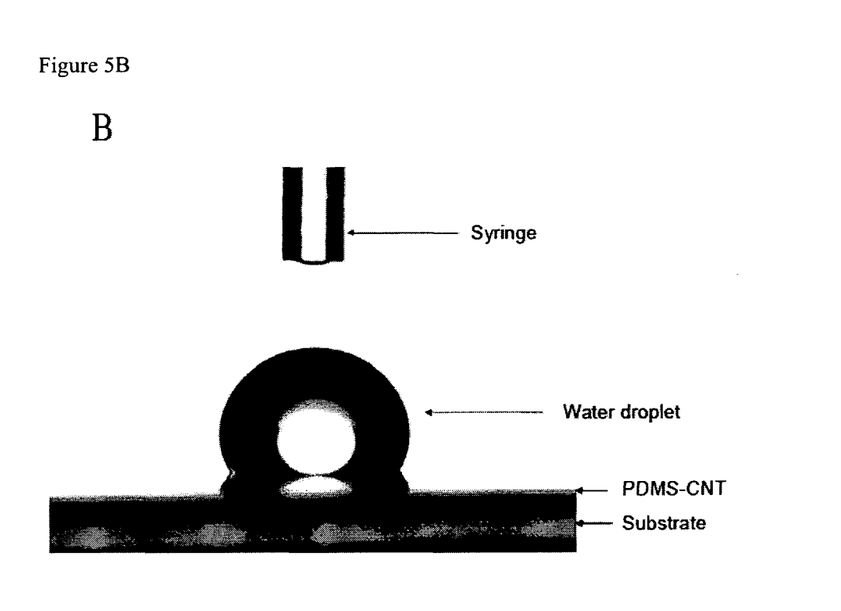

The silicone conduit can have both hydrophilic (attributed to functionalized CNT) and hydrophobic (attributed to silicone) properties. The hydrophilic or hydrophobic nature of the silicone-CNT conduit was analyzed using a tangential contact angle method by goniometry. A film having a silicone film coated with a thin functionalized CNT layer was prepared over a glass plate by the same method used for the preparation of the silicone conduit in a mold. The glass plate was used as a substrate for the preparation of the silicone-CNT film. The water contact angle experiment was performed on this film by placing a drop of water on the thin CNT layer on the silicone film. The CNT film surface of the silicone-CNT film exhibited hydrophobicity, which was estimated using goniometry. The increase in the CNT concentration increased the contact angle of the CNT film surface of the silicone-CNT film from about 113° to 120° (FIG. 5A). The silicone conduit possess both hydrophilic (attributed to functionalized CNT) and hydrophobic (attributed to silicone) properties. However, we did not observe significant decrease in water contact angle, even though carboxylic acid and hydroxyl group were present on the surface of CNT. This contrasting result may be attributed to the very thin layer of CNT on the surface of silicone. A contact angle greater than 90° indicates that the CNT surface of the silicone-CNT film has a hydrophobic nature as shown in FIG. 5A when a water droplet was placed on the CNT film of the silicone-CNT film (FIG. 5B). However, the hydrophobic nature of the silicone-CNT tube can be modified to hydrophilic by incorporating RGD peptides. In addition to their hydrophilicity, these peptides render more neuronal interactions with silicone conduits which in turn reduce any immunogenicity risks against the implanted NGC.

In FIG. 5A, 1 mg of functionalized CNT coated on silicone conduit did not have any significant change in contact angle over PDMS with no CNT treatment. When the amount of CNT treatment on silicone was gradually increased from zero mg (no CNT treatment) to 25 mg, with intermediate treatments of 2 mg, 5 mg and 10 mg (see PDMS CNT1 mg to PDMS CNT25 mg in FIG. 5A), the water contact angle was slightly increased to about 7 degrees versus that of an untreated silicone film. These results showed that the silicone layer had no major influence on the hydrophobicity of the CNT layer. However, as functionalized CNT has hydrophilic functional groups such as carboxylic and hydroxyl groups, functionalized CNT would be biocompatible.

In the detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes, but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general, such a construction is intended in the sense one having skill in the art would understand the convention (e.g., "a system having at least one of A, B, and C" would include, but not be limited to, systems that have A alone, B alone, C alone, A and B together, A and C together, B and C together, and/or A, B, and C together, etc.). In those instances where a convention analogous to "at least one of A, B, or C, etc." is used, in general, such a construction is intended in the sense one having skill in the art would understand the convention (e.g., "a system having at least one of A, B, or C" would include, but not be limited to, systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges, which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A conduit comprising an insulating material in a form of a tube having an inner surface and an outer surface, the inner surface comprising a film consisting of carbon nanotubes:
   wherein:
      the conduit is a nerve guide conduit
      the film is configured to conduct an electric current from a first end of the conduit attached to a first nerve stump to a second end of the conduit attached to a second nerve stump;
      the film has a thickness from 1 to 2 µm; and
      the carbon nanotubes comprise functionalized carbon nanotubes.

2. The conduit of claim 1, wherein the conduit has an electrical conducting property in a semi-conducting range at ambient conditions.

3. The conduit of claim 1, wherein the insulating material comprises silicone.

4. The conduit of claim 1, wherein the functionalized carbon nanotubes comprise carboxyl and hydroxyl functional groups.

5. The conduit of claim 1, comprising less than 1 wt % carbon nanotubes.

* * * * *